United States Patent [19]

Aloup et al.

[11] Patent Number: 5,677,306

[45] Date of Patent: Oct. 14, 1997

[54] DERIVATIVES OF 5H, 10H-IMIDAZO[1, 2-A] INDENO[1,2-E]PYRAZIN-4-ONE, PREPARATION THEREOF AND MEDICAMENTS CONTAINING THEM

[75] Inventors: Jean-Claude Aloup, Villeneuve Le Roi; François Audiau, Charenton Le Pont; Dominique Damour, Paris; Arielle Genevois-Borella, Thiais; Patrick Jimonet, Villepreux; Serge Mignani, Chatenay-Malabry, all of France

[73] Assignee: Rhone-Poulenc Rorer S.A., Antony, France

[21] Appl. No.: 406,982

[22] PCT Filed: Sep. 28, 1993

[86] PCT No.: PCT/FR93/00946

§ 371 Date: Mar. 31, 1995

§ 102(e) Date: Mar. 31, 1995

[87] PCT Pub. No.: WO94/07893

PCT Pub. Date: Apr. 14, 1994

[30] Foreign Application Priority Data

Oct. 2, 1992 [FR] France ................... 92 11674

[51] Int. Cl.⁶ ................... C07D 487/04; A61K 31/495
[52] U.S. Cl. ................... 514/250; 544/343
[58] Field of Search ................... 544/343; 514/250

[56] References Cited

U.S. PATENT DOCUMENTS

| 4,242,344 | 12/1980 | Lumma | 424/251 |
|---|---|---|---|
| 4,354,027 | 10/1982 | Loev et al. | 544/346 |
| 4,999,353 | 3/1991 | Watjen et al. | 514/250 |
| 5,166,155 | 11/1992 | Jorgensen et al. | 514/249 |
| 5,182,279 | 1/1993 | Jorgensen et al. | 514/250 |

FOREIGN PATENT DOCUMENTS

| 0 040 401 | 11/1981 | European Pat. Off. |
| 0 074 929 | 3/1983 | European Pat. Off. |
| 0 368 652 | 5/1990 | European Pat. Off. |
| 2 106 109 | 4/1983 | United Kingdom. |
| WO 91/13878 | 9/1991 | WIPO. |
| WO 91/16325 | 10/1991 | WIPO. |

OTHER PUBLICATIONS

Database WPI, Week 9232, Derwent Publ. Ltd., London, GB, AN 92–263039 & JP,A,4 178 385 (Yamanouchi Pharm. Co. Ltd.), Jun. 1992.

Chemical Abstracts, vol. 94, No. 19, 11 May 1981, Columbus, Ohio, abst. No. 156866p, E. Abignente et al.

Chemical Abstracts, vol. 107, No. 15, 12 Oct. 1987, Columbus, Ohio abstr. No. 134286, & J. Org. Chem. vol. 52, No. 19, pp. 4379–4381.

*Primary Examiner*—Mukund J. Shah
*Assistant Examiner*—King Lit Wong
*Attorney, Agent, or Firm*—Finnegan, Henderson, Farabow, Garrett & Dunner, L.L.P.

[57] ABSTRACT

Compounds having the formula (I) wherein R and $R_1$, similar or different, represent a hydrogen or halogen atom or a radical alkyl, alkoxy, amino, acylamino, phenylureido, $-N=CH-N(R_2)R_3$, nitro, imidazolyl, phenyl, $SO_3H$ or cyano; $R_2$ and $R_3$ which may be similar or different, represent each an alkyl radical; the invention also relates to the salts of such compounds, their preparation, intermediates for preparing them and drugs containing them.

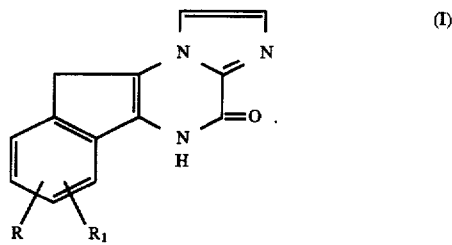

(I)

8 Claims, No Drawings

DERIVATIVES OF 5H, 10H-IMIDAZO[1, 2-A] INDENO[1,2-E]PYRAZIN-4-ONE, PREPARATION THEREOF AND MEDICAMENTS CONTAINING THEM

This application is the national stage of PCT/FR93/00946 filed Sep. 28, 1993.

The present invention relates to the compounds of formula:

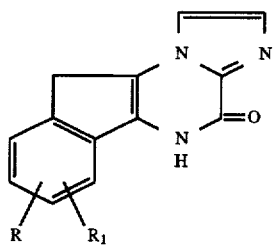

their salts, their preparation, the intermediates for preparing them and medicinal products containing them.

In formula (I), R and $R_1$, which are identical or different, represent a hydrogen or halogen atom or an alkyl, alkoxy, amino, acylamino, phenylureido, $-N=CH-N(R_2)R_3$, nitro, imidazolyl phenyl, $SO_3H$ or cyano radical, $R_2$ and $R_3$, which are identical or different, each represent an alkyl radical.

Unless otherwise stated, in the preceding definitions and in those which follow, the alkyl and alkoxy radicals contain 1 to 4 carbon atoms in a linear or branched chain and the acyl radicals and portions contain 2 to 5 carbon atoms. The halogen atoms are preferably bromine, chlorine and fluorine atoms.

The compounds of formula (I) for which R and/or $R_1$ represent a radical $-N=CH-N(R_2)R_3$, possess E and Z isomeric forms. These isomers and mixtures thereof form part of the invention.

The compounds of formula (I) may be prepared by dealkylation and desalification of the derivatives of formula:

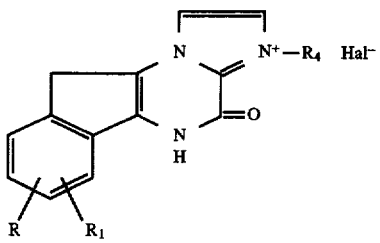

in which R and $R_1$ have the same meanings as in formula (I), $R_4$ represents an alkyl radical and Hal represents a halogen atom and, preferably, a bromine atom.

This reaction is preferably carried out in the presence of imidazole, at a temperature of between 100° and 200° C. and in particular at 160° C.

The derivatives of formula (II) are new and form part of the invention.

The derivatives of formula (II) may be obtained by the action of a derivative of formula:

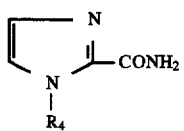

in which $R_4$ has the same meanings as in formula (II), on a 2-haloindanone of formula:

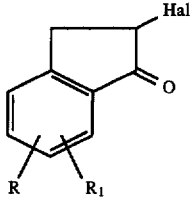

in which R and $R_1$ have the same meanings as in formula (I) and Hal represents a halogen atom and, preferably, a bromine atom.

This reaction is generally carried out in an inert solvent such as dimethylformamide, at a temperature of between 50° and 150° C. and, preferably, at 115° C.

The derivatives of formula (III) may be obtained by adapting or applying the method described by D. D. DAVEY, J. Org. Chem., 52, 4379 (1987).

The derivatives of formula (IV) may be obtained by halogenation of the corresponding indanones by means of a halogenating agent such as bromine or chlorine, in an inert solvent such as a chlorine-containing solvent (for example methylene chloride or chloroform), at a temperature of −15° C. or in acetic acid, at a temperature close to 20° C., or a copper halide, in dioxane, at a temperature close to 100° C. or by applying or adapting the methods described by K. MORI, Agr. Biol. Chem., 27 (1), 22 (1963); J. CHAKRAVARTY, Indian J. Chem., 7 (3), 215 (1969), F. G. HOLLIMAN et al., J. Chem. Soc., 9 (1960), D. MUKHOPADHYA et al., J. Indian Chem. Soc., 47 (5), 450 (1970) and in Patents DE 2640358 and EP 346107 and in the examples.

The indanones may be obtained by applying or adapting the methods described by M. OLIVIER et al., Bull. Soc. Chim. de France, 3092 (1973), R. SEKA et al., Chem. Ber., 75B, 1730 (1942), in U.S. Pat. Nos. 4,263,319, 4,096,173 and EP 314400 and in the examples.

The compounds of formula (I) may also be prepared by cyclization of a derivative of formula:

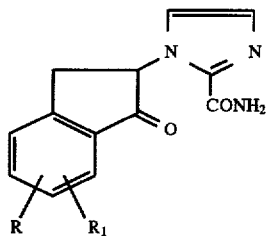

in which R and $R_1$ have the same meanings as in formula (I).

This cyclization is carried out by means of an acid such as acetic acid or hydrochloric acid, in aqueous medium or in an alcohol such as ethanol or methanol, optionally in the presence of ammonium acetate, at the boiling temperature of the reaction medium.

The derivatives of formula (V) may be obtained by the action of ammonia on a derivative of formula:

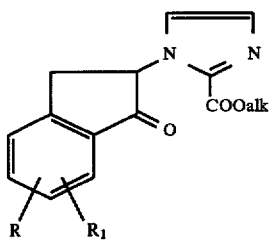

in which R and $R_1$ have the same meanings as in formula (I) and alk represents an alkyl radical.

This reaction is carried out in an alcohol such as methanol or ethanol, at a temperature of between 20° C. and the boiling temperature of the reaction medium.

The derivatives of formula (VI) may be obtained by the action of a 2-haloindanone of formula (IV) on a derivative of formula:

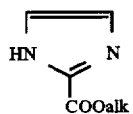

in which alk has the same meanings as in formula (VI).

This reaction is carried out either by fusion at a temperature of between 130° and 180° C., or in an inert solvent such as dimethylformamide in the presence of a base such as an alkali metal hydride (for example sodium hydride), at a temperature close to 20° C., or in an inert solvent such as a chlorine-containing solvent such as chloroform in the presence of a nitrogen-containing organic base (for example 1,8-diazabicyclo[5.4.0]undec-7-ene), at a temperature close to 20° C., or in an inert solvent such as an alcohol (for example ethanol or propanol), an aromatic solvent such as toluene, a chlorine-containing solvent (for example chloroform), optionally in the presence of sodium iodide, at the boiling temperature of the reaction medium.

The derivatives of formula (VII) may be obtained by applying or adapting the method described in U.S. Pat. No. 3,600,399.

The compounds of formula (I) for which R and/or $R_1$ represent a nitro radical may also be prepared by nitration of a corresponding compound of formula (I) for which R and/or $R_1$ represent a hydrogen atom.

This nitration is generally carried out by means of a nitrating agent such as an alkali metal nitrate (preferably potassium nitrate), in sulphuric acid at a temperature of 0° C. to 30° C.

The compounds of formula (I) for which R and/or $R_1$ represent an amino radical may also be prepared by reducing a corresponding compound of formula (I) for which R and/or $R_1$ represent a nitro radical.

This reduction is generally carried out by means of hydrogen, at a pressure of 1 to 2 bar, in the presence of aqueous sodium hydroxide and a catalyst such as palladium on carbon, at a temperature close to 20° C.

The compounds of formula (I) for which R and/or $R_1$ represent an $SO_3H$ radical may also be prepared by sulphonating a corresponding derivative of formula (I) for which R and/or $R_1$ represent a hydrogen atom.

This reaction is generally carried out by means of chlorosulphonic acid, at a temperature of between 0° and 20° C.

The compounds of formula (I) for which R and/or $R_1$ represent an acylamino radical may also be prepared by acylating a corresponding compound of formula (I) for which R and/or $R_1$ represent an amino radical.

This acylation is generally carried out in an inert solvent such as dimethylformamide, by means of an acid anhydride (alk-CO)$_2$O in which alk represents an alkyl radical containing 1 to 4 carbon atoms, in the presence of a base such as a trialkylamine (for example triethylamine), at the boiling temperature of the reaction medium.

The compounds of formula (I) for which R and/or $R_1$ represent a phenylureido radical may also be prepared by the action of phenyl isocyanate on a corresponding compound of formula (I) for which R and/or $R_1$ represent an amino radical.

This reaction is generally carried out in an inert solvent such as dimethyl sulphoxide, dimethylformamide, a chlorine-containing solvent (for example chloroform), in the presence of a base such as a trialkylamine (for example triethylamine), at a temperature close to 20° C.

The compounds of formula (I) for which R and/or $R_1$ represent a radical —N=CH—N($R_2$)$R_3$ may also be prepared by the action of a corresponding compound of formula (I) for which R and/or $R_1$ represent an amino radical on an amide HCO—N($R_2$)$R_3$ in which $R_2$ and $R_3$ have the same meanings as in formula (I).

This reaction is preferably carried out in the presence of methylsulphonyl chloride and a base such as a trialkylamine (for example triethylamine), at a temperature close to 20° C.

The compounds of formula (I) may be purified by the usual known methods, for example by crystallization, chromatography or extraction.

The E and Z isomers of the compounds of formula (I) for which R and/or $R_1$ represent a radical —N=CH—N($R_2$)$R_3$ may be separated by the usual known methods, for example by crystallization or chromatography.

The compounds of formula (I) containing a basic residue may be optionally converted to addition salts with an inorganic or organic acid by the action of such an acid in an organic solvent such as an alcohol, a ketone, an ether or a chlorine-containing solvent.

The compounds of formula (I) containing an acidic residue may be optionally converted to metallic salts or to addition salts with nitrogen-containing bases according to methods known per se. These salts may be obtained by the action of a metallic (for example alkali metal or alkaline-earth metal) base, ammonia, an amine or a salt of an amine on a compound of formula (I), in a solvent. The salt formed is separated by the usual methods.

These salts also form part of the invention.

As examples of pharmaceutically acceptable salts, there may be mentioned the addition salts with inorganic or organic acids (such as acetate, propionate, succinate, benzoate, fumarate, maleate, oxalate, methanesulphonate, isethionate, theophyllinacetate, salicylate, methylene-bis-β-oxynaphthoate, hydrochloride, sulphate, nitrate and phosphate), the salts with alkali metals (sodium, potassium and lithium) or with alkaline-earth metals (calcium and magnesium), the salt of ammonium, the salts of nitrogen-containing bases (ethanolamine, trimethylamine, methylamine, benzylamine, N-benzyl-β-phenethylamine, choline, arginine, leucine, lysine, N-methylglucamine).

The compounds of formula (I) have useful pharmacological properties. These compounds are antagonists of the α-amino-3-hydroxy-5-methyl- 4-isoxazolepropionic acid (AMPA) receptor, also known as quisqualate receptor.

Moreover, the compounds of formula (I) are non-competitive antagonists of the N-methyl-D-aspartate (NMDA) receptor and, more particularly, they are ligands for the glycine modulating sites of the NMDA receptor.

These compounds are therefore useful for treating or preventing all ischemias (such as focal or global ischemia)

following cerebral vascular accidents, a cardiac arrest, an arterial hypotension, a cardiac or pulmonary surgical operation or a severe hypoglycemia. They are generally useful in the treatment of effects due to an anoxia, whether perinatal or following a drowning or cerebrospinal lesions. These compounds may also be used for treating or preventing the progression of neurodegenerative diseases, of HUNTINGTON'S chorea, of ALZHEIMER'S disease, of amyotrophic lateral sclerosis, of olivopontocerebellar atrophy and of PARKINSON'S disease. These compounds may also be used against epileptogenic and/or convulsive manifestations, for the treatment of cerebral and spinal traumas, for the treatment of anxiety (KEHNE et al., Eur. J. Pharmacol., 193, 283 (1991), depression (TRULLAS et al., Eur. J. Pharmacol., 185, 1 (1990), schizophrenia (REYNOLDS, TIPS, 13, 116 (1992), as analgesics (DICKENSON et al., Neurosc. Letters, 121, 263 (1991), antianoretics (SORRELS et al., Brain Res., 572, 265 (1992), antimigraines, antiemetics and for treating poisoning by neurotoxins or other substances which are NMDA receptor agonists, as well as neurological disorders associated with viral diseases such as aids (LIPTON et al., Neuron, 7, 111 (1991)), rabies, measles and tetanus (BAGETTA et al., Br. J. Pharmacol., 101, 776 (1990). These compounds are also useful for the prevention of drug and alcohol withdrawal symptoms and inhibition of acquired tolerance of and dependency on opiates.

The affinity of the compounds of formula (I) for the AMPA receptor was determined by studying the antagonism of the specific binding of [$^3$H]-AMPA to rat cerebral cortex membranes (HONORE et al., Neuroscience letters, 54, 27 (1985)). [$^3$H]-AMPA is incubated in the presence of 0.2 mg of proteins at 4° C. for 30 minutes in 10 mM $KH_2PO_4$, 100 mM KSCN buffer, pH 7.5. Non-specific binding is determined in the presence of 1 mM L-glutamate. The bound radioactivity is separated by filtration on PHARMACIA filters (Printed Filtermate A). The inhibitory activity of these products is generally less than 100 μm.

The affinity of the compounds of formula (I) for the glycine site linked to the NMDA receptor was determined by studying the antagonism of the specific binding of [$^3$H]-DCKA to rat cerebral cortex membranes according to the method described by T. CANTON et al., J. Pharm. Pharmacol., 44, 812 (1992). [$^3$H]-DCKA (20 nM) is incubated in the presence of 0.1 mg of proteins at 4° C. for 30 minutes in 50 mM HEPES buffer, pH 7.5. Non-specific binding is determined in the presence of 1 mM glycine. The bound radioactivity is separated by filtration on Whatman GF/B filters. The inhibitory activity of these products is generally less than 100 μM.

The compounds of formula (I) have a low toxicity. Their $LD_{50}$ is greater than 50 mg/kg by the IP route in mice.

The preferred compounds of formula (I) are those for which either R represents a hydrogen atom and $R_1$ is in position 7, 8 or 9 and represents a hydrogen or halogen atom or an alkyl, alkoxy, amino, acylmmino, phenylureido, —N=CH—N($R_2$)$R_3$, nitro, imidazolyl, phenyl or $SO_3H$ radical; or R represents a halogen atom and $R_1$ represents a halogen atom or a nitro radical.

EXAMPLES

Example 1

1.8 g of 1-(5-fluoro-1-oxo-2-indanyl)-imidazole-2-carboxamide is dissolved in 90 ml of boiling methanol and the solution, supplemented with 0.1 g of decolorizing charcoal, is filtered. The filter is washed with 20 ml of boiling methanol and then the filtrate and the washing are pooled, supplemented with 27 ml of 12N aqueous hydrochloric acid solution and kept for 3 hours at 5° C. The crystals are separated by filtration, washed twice with a total of 20 ml of ice-cold methanol and dried under reduced pressure (1 mmHg; 0.13 kPa) at 60° C. 1 g of 8-fluoro-5H, 10H-imidazo[1,2-a]indeno[1,2-e]pyrazin-4-one hydrochloride is thus obtained which decomposes without melting above 300° C. [NMR spectrum: (200 MHz; DMSO-d$_6$; δ in ppm): 4.11 (s, 2H: —CH2— in position 10); 7.32 (ddd, J=9.5–8.5 and 2 Hz, 1H: —H7); 7.57 (dd, J=9.5 and 2 Hz, 1H: —H9); 7.97 (dd, j=8.5 and 5 Hz, 1H: —H6); 7.99 and 8.28 (2d, J=1.5 Hz, 1H each: —H of imidazole); 13.13 (unresolved complex, 1H: —CONH—)].

The 1-(5-fluoro-1-oxo-2-indanyl)imidazole-2-carboxamide can be prepared in the following manner: 2.2 g of ethyl 1-(5-fluoro-1-oxo-2-indanyl)imidazole-2-carboxylate are dissolved in 80 ml of a 2.5N ammoniacal methanol solution and the solution is kept for 20 hours at a temperature close to 20° C. and then concentrated to dryness under reduced pressure (15 mmHg; 2 kPa) at 35° C. The product obtained is suspended in 50 ml of isopropyl ether, filtered, washed twice with a total of 20 ml of isopropyl ether and then dried under reduced pressure (15 mmHg; 2 kPa) at a temperature close to 20° C. 1.85 g of 1-(5-fluoro-1-oxo-2-indanyl)imidazole-2-carboxamide are thus obtained in the form of a solid which melts at 221° C.

The ethyl 1-(5-fluoro-1-oxo-2-indanyl)-imidazole-2-carboxylate can be prepared in the following manner: a solution of 13.3 g of ethyl imidazole-2-carboxylate in 145 ml of anhydrous dimethylformamide is added dropwise over 20 minutes at a temperature of between 20° C. and 25° C. to a suspension of 3.4 g of 80% sodium hydride in 45 ml of anhydrous dimethylformamide maintained under a nitrogen atmosphere. After stirring for 15 minutes, a solution of 26 g of 2-bromo-5-fluoro-1-indanone in 190 ml of anhydrous dimethylformamide is added dropwise over 10 minutes at the same temperature. The mixture is stirred for 1 hour 30 minutes and then, after slow addition of 100 ml of water, poured over 3800 ml of distilled water and extracted 4 times with a total of 3800 ml of chloroform. The organic extracts are pooled, washed with 950 ml of distilled water, dried over anhydrous sodium sulphate and concentrated to dryness under reduced pressure (15 mmHg; 2 kPa) at 40° C. The product obtained (27 g) is chromatographed on 1490 g of neutral silica gel (0.020–0.045 mm) contained in a column 9.6 cm in diameter, eluting under pressure with a dichloromethane-ethyl acetate mixture (70–30 by volume) and collecting 80 ml fractions. Fractions 13 to 70 are pooled and concentrated to dryness under reduced pressure (15 mmHg; 2 kPa) at 40° C. 13.4 g of ethyl 1-(5-fluoro-1-oxo-2-indanyl)imidazole-2-carboxylate are thus obtained which melt at 127° C.

The 2-bromo-5-fluoro-1-indanone can be prepared in the following manner: a solution of 20.6 g of bromine in 90 ml of acetic acid is added dropwise over 1 hour at 20° C. to a solution of 20 g of 5-fluoro-1-indanone and 0.1 ml of a 47% aqueous hydrobromic acid solution in 260 ml of acetic acid. After stirring for 2 hours, the mixture is poured over 850 ml of distilled water and extracted 3 times with a total of 850 ml of methylene chloride. The organic extracts are pooled, washed with 200 ml of distilled water, dried over anhydrous sodium sulphate and concentrated to dryness under reduced pressure (15 mmHg; 2 kPa) at 30° C. The product obtained (31 g) is chromatographed on 1860 g of neutral silica gel (0.020–0.045 mm) contained in a column 9.8 cm in diameter, eluting with a cyclohexane-ethyl acetate mixture (70–30 by volume) and collecting a fraction of 10.5 litres which is removed and then a fraction of 25 liters which is concentrated under reduced pressure (15 mmHg; 2 kPa) at 40° C. 28.4 g of 2-bromo-5-fluoro-1-indanone are thus obtained in the form of a yellow oil [Rf=0.7; thin-layer chromatography on silica gel; solvent: cyclohexane-ethyl acetate (70–30 by volume)].

Example 2

The procedure is carried out as in Example 1 but starting with 1.8 g of 1-(5-methyl-1-oxo-2-indanyl)imidazole-2-carboxamide, a total of 80 ml of methanol and 22 ml of 12N aqueous hydrochloric acid solution. 1.5 g of 8-methyl-5H, 10H-imidazo [1,2-a]indeno[1,2-e]pyrazin-4-one hydrochloride are thus obtained which decompose without melting above 300° C. [NMR spectrum: (200 MHz; DMSO-$d_6$; δ in ppm): 2.42 (s, 3H: Ar—C$\underline{H}$3); 4.05 (s, 2H: —C$\underline{H}$2— in position 10); 7.27 (broad d, J=8 Hz 1H: —$\underline{H}$7); 7.48 (broad s, 1H: —$\underline{H}$9); 7.83 (d, J=8 Hz, 1H: —$\underline{H}$6); 7.97 and 8.25 (2d, J=1.5 Hz, 1H each: —$\underline{H}$ of imidazole); 13.20 (unresolved complex, 1H: —CON$\underline{H}$—)].

The 1-(5-methyl-1-oxo-2-indanyl)imidazole-2-carboxamide can be prepared as in Example 1 for the preparation of 1-(5-fluoro-1-oxo-2-indanyl)imidazole-2-carboxamide but starting with 2.4 g of ethyl 1-(5-methyl-1-oxo-2-indanyl)imidazole-2-carboxylate and 75 ml of a 2.5N ammoniacal methanol solution. 1.9 g of 1-(5-methyl-1-oxo-2-indanyl)imidazole-2-carboxamide are thus obtained in the form of a solid which melts at 196° C.

The ethyl 1-(5-methyl-1-oxo-2-indanyl)imidazole-2-carboxylate can be prepared as in Example 1 for the preparation of ethyl 1-(5-fluoro-1-oxo-2-indanyl)imidazole-2-carboxylate but starting with 2.24 g of ethyl imidazole-2-carboxylate, 0.6 g of 80% sodium hydride, 4.6 g of 2-bromo-5-methyl-1-indanone and a total of 62 ml of anhydrous dimethylformamide. After silica gel chromatography with a dichloromethane-ethyl acetate mixture (80–20 by volume), 2.5 g of ethyl 1-(5-methyl-1-oxo-2-indanyl)imidazole-2-carboxylate are obtained which melt at 131° C.

The 2-bromo-5-methyl-1-indanone can be prepared as in Example 1 for the preparation of 2-bromo-5-fluoro-1-indanone but starting with 7.3 g of 5-methyl-1-indanone, 8 g of bromine, 0.05 ml of a 47% aqueous hydrobromic acid solution and a total of 165 ml of acetic acid. After silica gel chromatography with a cyclohexane-dichloromethane mixture (70–30 by volume), 4.6 g of 2-bromo-5-methyl-1-indanone are obtained which melt at 54° C.

Example 3

The procedure is carried out as in Example 1 but starting with 2 g of 1-(4-methyl-1-oxo-2-indanyl)imidazole-2-carboxamide, a total of 60 ml of methanol and 25 ml of 12N aqueous hydrochloric acid solution. 1.45 g of 9-methyl-5H, 10H-imidazo [1,2-a]indeno[1,2-e]pyrazin-4-one hydrochloride are thus obtained which decompose without melting above 300° C. [NMR spectrum: (300 MHz; DMSO-$d_6$ plus a few drops of CD3COOD-$d_4$; δ in ppm): 2.40 (s, 3H: —C$\underline{H}$3); 4.01 (s, 2H: —C$\underline{H}$2— in position 10); 7.23 (d, J=8 Hz 1H: —$\underline{H}$8); 7.36 (t, J=8 Hz, 1H: —$\underline{H}$7); 7.8 (d, J=8 Hz, 1H: —$\underline{H}$6); 8.17 and 8.36 (2d, J=1 Hz, 1H each: —$\underline{H}$ of imidazole).

The 1-(4-methyl-1-oxo-2-indanyl)imidazole-2-carboxamide can be prepared as in Example 1 for the preparation of 1-(5-fluoro-1-oxo-2-indanyl)imidazole-2-carboxamide but starting with 2.7 g of ethyl 1(4-methyl-1-oxo-2-indanyl)imidazole-2-carboxylate and 160 ml of a 2.5N ammoniacal methanol solution. 2.1 g of 1-(4-methyl-1-oxo-2-indanyl)imidazole-2-carboxamide are thus obtained in the form of a solid which melts at 160° C.

The ethyl-1-(4-methyl-1-oxo-2-indanyl)-imidazole-2-carboxylate can be prepared as in Example 1 for the preparation of ethyl 1-(5-fluoro-1-oxo-2-indanyl)imidazole-2-carboxylate but starting with 2.8 g of ethyl imidazole-2-carboxylate, 0.7 g of 80% sodium hydride, 4.6 g of 2-bromo-4-methyl-1-indanone and a total of 75 ml of anhydrous dimethylformamide. After silica gel chromatography with a dichloromethane-ethyl acetate mixture (80–20 by volume), 2.8 g of ethyl 1-(4-methyl-1-oxo-2-indanyl)imidazole-2-carboxylate are obtained which melt at 123° C.

The 2-bromo-4-methyl-1-indanone can be prepared as described by K. MORI, Agr. Biol. Chem., 27 (1), 22 (1963).

Example 4

The procedure is carried out as in Example 1 but starting with 1 g of 1-(6-chloro-1-oxo-2-indanyl)imidazole-2-carboxamide, a total of 75 ml of methanol and 15 ml of 12N aqueous hydrochloric acid solution. 0.4 g of 7-chloro-5H, 10H-imidazo [1,2-a]indeno[1,2-e]pyrazin-4-one hydrochloride is obtained which decomposes without melting above 300° C. [NMR spectrum: (300 MHz; DMSO-$d_6$; δ in ppm): 4.12 (s, 2H: —C$\underline{H}$2— in position 10); 7.44 (dd, J=8 and 1 Hz 1H: —$\underline{H}$8); 7.66 (d, J=8 Hz, 1H: —$\underline{H}$9); 7.95 and 8.25 (2s broad, 1H each: —$\underline{H}$ of imidazole); 8.05 (d, j=1 Hz, 1H: —$\underline{H}$6); 12.97 (unresolved complex, 1H: —CON$\underline{H}$—)].

The 1-(6-chloro-1-oxo-2-indanyl)imidazole-2-carboxamide can be prepared as in Example 1 for the preparation of 1-(5-fluoro-1-oxo-2-indanyl)imidazole-2-carboxamide but starting with 1.2 g of ethyl 1-(6-chloro-1-oxo-2-indanyl)imidazole-2-carboxylate and 45 ml of a 2.5N ammoniacal methanol solution. 1 g of 1-(6-chloro-1-oxo-2-indanyl)imidazole-2-carboxamide is thus obtained in the form of a solid which melts at 190° C.

The ethyl 1-(6-chloro-1-oxo-2-indanyl)imidazole-2-carboxylate can be prepared as in Example 1 for the preparation of ethyl 1-(5-fluoro-1-oxo-2-indanyl)imidazole-2-carboxylate but starting with 2.5 g of ethyl imidazole-2-carboxylate, 0.7 g of 80% sodium hydride, 5.4 g of 2-bromo-6-chloro-1-indanone and a total of 70 ml of anhydrous dimethylformamide. After silica gel chromatography with a dichloromethane-ethyl acetate mixture (70–30 by volume), 1 g of ethyl 1-(6-chloro-1-oxo-2-indanyl)imidazole-2-carboxylate is obtained which melts at 180° C.

The 2-bromo-6-chloro-1-indanone can be prepared as described in German Patent 2,640,358.

Example 5

The procedure is carried out as in Example 1 but starting with 0.84 g of 1-(5-chloro-1-oxo- 2-indanyl)imidazole-2-carboxamide, a total of 55 ml of methanol and 4 ml of a 12N aqueous hydrochloric acid solution. 0.64 g of 8-chloro-5H, 10H-imidazo[1,2-a]indeno[1,2-e]pyrazin-4-one hydrochloride is thus obtained which decomposes without melting above 300° C. [NMR spectrum: (200 MHz; DMSO-$d_6$; δ in ppm): 4.07 [s, 2H: —C$\underline{H}$2— in position 10 (observed in DMSO-$d_6$ plus a few drops of CD3COOD-$d_4$)]; 7.55 (dd, J=8 and 2 Hz 1H: —$\underline{H}$7); 7.76 (d, J=2 Hz, 1H: —$\underline{H}$9); 7.95 (d, J=8 Hz, 1H: —$\underline{H}$6); 7.95 and 8.25 (2d, J=1.5 Hz, 1H each: —$\underline{H}$ of imidazole); 13.00 (unresolved complex, 1H: —CON$\underline{H}$—)].

The 1-(5-chloro-1-oxo-2-indanyl)imidazole-2-carboxamide can be prepared in the following manner: a solution of 1.2 g of ethyl 1-(5-chloro-1-oxo-2-indanyl) imidazole-2-carboxylate in 45 ml of methanol is maintained saturated for 6 hours, with boiling, with a stream of azunonia gas. After cooling to 5° C., the crystals are separated by filtration, washed with 1 ml of ice-cold methanol and air dried at 20° C. 0.4 g of 1-(5-chloro-1-oxo-2-indanyl) imidazole-2-carboxamide is thus obtained in the form of a solid which melts at 240° C.

The ethyl 1-(5-chloro-1-oxo-2-indanyl)imidazole-2-carboxylate can be prepared in the following manner: a solution of 3.65 g of 1,8-diazabicyclo[5.4.0]undec-7-ene in 10 ml of chloroform is added dropwise over 20 minutes at a temperature close to 20° C. to a solution of 2.8 g of ethyl imidazole-2-carboxylate and 6.1 g of 2-bromo-5-chloro-1-indanone. After stirring for 2 hours and adding 100 ml of distilled water, the mixture is extracted 3 times with a total of 75 ml of chloroform and the organic extracts are pooled, dried over anhydrous magnesium sulphate and concentrated to dryness under reduced pressure (15 mmHg; 2 kPa) at 50° C. After silica gel chromatography with a dichloromethane-ethyl acetate mixture (70–30 by volume), 1 g of ethyl 1-(5-chloro-1-oxo-2-indanyl)imidazole-2-carboxylate is obtained in the form of a thick yellow oil [Rf=0.3, thin-layer chromatography on silica gel; solvent: dichloromethane-ethyl acetate (70–30 by volume)].

The 2-bromo-5-chloro-1-indanone can be prepared as described in German Patent 2,640,358.

Example 6

The procedure is carried out as in Example 1 but starting with 1.4 g of 1-(4-chloro-1-oxo-2-indanyl)imidazole-2-carboxamide, a total of 70 ml of methanol and 21 ml of a 12N aqueous hydrochloric acid solution. 0.53 g of 9-chloro-5H, 10H-imidazo [1,2-a]indeno[1,2-e]pyrazin-4-one is thus obtained which decomposes without melting above 300° C. [NMR spectrum: (200 MHz; DMSO-$d_6$; δ in ppm): 4.06 (s, 2H: —C$\underline{H}$2— in position 10); 7.40 (dd, J=8 and 1 Hz 1H: —$\underline{H}$8); 7.49 (t, J=8 Hz, 1H: —$\underline{H}$7); 7.61 and 8.08 (2d, J=1 Hz, 1H each: —$\underline{H}$ of imidazole); 7.85 (d, J=8 Hz, 1H: —$\underline{H}$6); 2.47 (unresolved complex, 1H, —CON$\underline{H}$—)].

The 1-(4-chloro-1-oxo-2-indanyl)imidazole-2-carboxamide can be prepared in the following manner: a solution of 1.8 g of ethyl 1-(4-chloro-1-oxo-2-indanyl) imidazole-2-carboxylate in 170 ml of a 2.5N ammoniacal methanol solution is kept for 16 hours at a temperature close to 20° C. and then concentrated to dryness under reduced pressure (15 mmHg; 2 kPa) at 50° C. The product obtained is suspended in 30 ml of isopropyl ether, filtered, washed twice with a total of 10 ml of isopropyl ether and then dried under reduced pressure (15 mmHg; 2 kPa) at a temperature close to 20° C. 1.4 g of 1-(4-chloro-1-oxo-2-indanyl) imidazole-2-carboxamide are thus obtained in the form of a solid which melts at 90° C.

The ethyl 1-(4-chloro-1-oxo-2-indanyl)-imidazole-2-carboxylate can be prepared as in Example 1 for the preparation of ethyl 1-(5-fluoro-1-oxo-2-indanyl)imidazole-2-carboxylate but starting with 2.8 g of ethyl imidazole-2-carboxylate, 0.6 g of 80% sodium hydride, 6.4 g of 2-bromo-4-chloro-1-indanone and a total of 80 ml of anhydrous dimethylformamide. After silica gel chromatography with a dichloromethane-ethyl acetate mixture (80–20 by volume), 1.85 g of ethyl 1-(4-chloro-1-oxo-2-indanyl)imidazole-2-carboxylate are obtained [Rf=0.3, thin-layer chromatography on silica gel; solvent: dichloromethane-ethyl acetate (80–20 by volume)].

The 2-bromo-4-chloro-1-indanone can be prepared in the following manner: a solution of 16 g of bromine in 45 ml of acetic acid is added dropwise over 30 minutes at a temperature close to 20° C. to a suspension of 17.5 g of 4-chloro-1-indanone in a mixture of 240 ml of acetic acid and 0.1 ml of a 47% aqueous hydrobromic acid solution. After stirring for 2 hours at the same temperature, the mixture is poured over 380 ml of distilled water. The crystals are separated hy filtration, washed twice with a total of 60 ml of distilled water and dried under reduced pressure (15 mmHg; 2 kPa) at 45° C. The product obtained (19.3 g) is suspended in 60 ml of petroleum ether, filtered, washed with 10 ml of petroleum ether and dried under reduced pressure (15 mmHg; 2 kPa) at 45° C. 14.7 g of 2-bromo-4-chloro-1-indanone are thus obtained which melt at 72° C.

The 4-chloro-1-indanone can be prepared as described in U.S. Pat. No. 4,096,173.

Example 7

The procedure is carried out as in Example 1 but starting with 0.5 g of 1-(4-phenyl-1-oxo-2-indanyl)imidazole-2-carboxamide, a total of 60 ml of methanol and 8 ml of a 12N aqueous hydrochloric acid solution. 0.35 g of 9-phenyl1-5H, 10H-imidazo [1,2-a]indeno[1,2-e]pyrazin-4-one hydrochloride is thus obtained which decomposes without melting above 300° C. [NMR spectrum: (300 MHz; DMSO-$d_6$; δ in ppm): 4.16 (s, 2H: —C$\underline{H}$2— in position 10); 7.41 and 7.98 (2dd, j=8 and 1 Hz, 1H each: —$\underline{H}$6 and —$\underline{H}$8); 7.47 (broad t, J=8 Hz, 1H: aromatic in the para position of the phenyl); 7.55 (t, J=8 Hz, 1H: —$\underline{H}$7); 7.58 (broad t, J=8 Hz, 2H: aromatics in the meta position of the phenyl); 7.67 (broad d, J=8 Hz, 2H: aromatics in the ortho position of the phenyl); 7.91 and 8.26 (2d, J=1 Hz, 1H each: —$\underline{H}$ of imidazole); 13.00 (unresolved complex 1H, —CON$\underline{H}$—)].

The 1-(4-phenyl-1-oxo-2-indanyl)imidazole-2-carboxamide can be prepared as in Example 1 for the preparation of 1-(5-fluoro-1-oxo-2-indanyl)imidazole-2-carboxamide but starting with 0.64 g of ethyl 1-(5-methyl-1-oxo-2-indanyl)imidazole-2-carboxylate and 80 ml of a 5N ammoniacal methanol solution. 0.5 g of 1-(4-phenyl-1-oxo-2-indanyl)imidazole-2-carboxamide is thus obtained in the form of a solid which melts at 196° C.

The ethyl 1-(4-phenyl-1-oxo-2-indanyl)imidazole-2-carboxylate can be prepared in the following manner: a mixture of 1.1 g of ethyl imidazole-2-carboxylate and 1.15 g of 2-bromo-4-phenyl-1-indanone is heated for 20 minutes at 130° C., cooled to 20° C. and dissolved in 25 ml of dichloromethane. The solution is washed with 10 ml of distilled water and, after decanting, the aqueous phase is extracted twice with a total of 20 ml of dichloromethane. The organic phases are pooled, washed with 10 ml of a saturated sodium hydrogen carbonate solution, twice with a total of 20 ml of distilled water, dried over anhydrous sodium sulphate and concentrated to dryness under reduced pressure (15 mmHg; 2 kPa) at 35° C. The product obtained (1.55 g) is chromatographed on 155 g of neutral silica gel (0.020–0.045mm) contained in a column 3.3 cm in diameter, eluting under pressure with a dichloromethane-ethyl acetate mixture (80–20 by volume) and collecting 10-ml fractions. Fractions 72 to 140 are pooled and concentrated to dryness under reduced pressure (15 mmHg; 2 kPa) at 40° C. 0.55 g of ethyl 1-(4-phenyl-1-oxo-2-indanyl)imidazole-2-carboxylate is thus obtained which melts at 185° C.

The 2-bromo-4-phenyl-1-indanone can be prepared as in Example 1 for the preparation of 2-bromo-5-fluoro-1-indanone but starting with 2.65 g of 4-phenyl-1-indanone, 2 g of bromine, 0.1 ml of a 47% aqueous hydrobromic acid solution and a total of 55 ml of acetic acid. After silica gel chromatography with a cyclohexane-dichloromethane mixture (50–50 by volume), 2.1 g of 2-bromo-4-phenyl-1-indanone are obtained which melt at 98° C.

The 4-phenyl-1-indanone can be prepared as described in U.S. Pat. No. 4,263,319.

Example 8

The procedure is carried out as in Example 1 but starting with 0.46 g of 1-[5-(1-imidazolyl)-1-oxo-2-indanyl] imidazole-2-carboxamide, a total of 35 ml of methanol and 7 ml of a 12N aqueous hydrochloric acid solution. 0.23 of 8-(1-imidazolyl)-5H, 10H-imidazo[1,2-a]indeno[1,2-e] pyrazine-4-one hydrochloride is thus obtained which decomposes without melting above 300° C. [NMR spectrum: (200 MHz; DMSO-$d_6$; δ in ppm): 4.18 (s, 2H: —C$\underline{H}$2— in position 10); 7.71 and from 8.00 to 8.15 (broad s and mt respectively, 1H for the s: —$\underline{H}$ of imidazole); 7.88 (dd, J=8 and 2 Hz 1H: —$\underline{H}$7); 7.96 and 8.34 (2 mt, 1H each: —$\underline{H}$4' and —$\underline{H}$5' of imidazole in position 8); 8.08 (d, J=8 Hz: —$\underline{H}$6); from 8.00 to 8.15 (mt: —$\underline{H}$9); 9.73 (broad s, 1H: —$\underline{H}$2' of imidazole in position 8); 12.65 (unresolved complex, 1H: —CON$\underline{H}$—)].

The 1-[5-(1-imidazolyl)-1-oxo-2-indanyl]-imidazole-2-carboxamide can be prepared as in Example 1 for the preparation of 1-(5-fluoro-1-oxo-2-indanyl)imidazole-2-carboxamide but starting with 0.6 g of ethyl 1-[5-(1-imidazolyl)-1-oxo-2-indanyl]imidazole-2-carboxylate and 30 ml of a 2.5N ammoniacal methanol solution. 0.46 g of 1-[5-(1-imidazolyl)-1-oxo-2-indanyl]imidazole-2-carboxamide is thus obtained in the form of a solid which melts at 140° C.

The ethyl 1-[5-(1-imidazolyl)-1-oxo-2-indanyl] imidazole-2-carboxylate can be prepared in the following manner: 1.1 g of bromine is added at 70° C. to a solution of 1.2 g of 5-(1-imidazolyl)-1-indanone in a mixture of 10 ml of acetic acid and 0.5 ml of a 47% aqueous hydrobromic acid solution. After stirring for 30 minutes at the same temperature, the mixture is poured over 50 ml of distilled water, neutralized by adding 15 g of sodium carbonate and extracted 4 times with a total of 90 ml of dichloromethane. The organic extracts are pooled, washed with 20 ml of a saturated aqueous sodium chloride solution, dried over anhydrous sodium sulphate, supplemented with 10 ml of anhydrous dimethylformamide and the dichloromethane is selectively removed under reduced pressure (15 mmHg; 2 kPa) at 40° C. The solution in dimethylformamide thus obtained (10 ml) is added dropwise over 5 minutes at 25° C. to a solution of 0.7 g of ethyl imidazole-2-carboxylate in 10 ml of anhydrous dimethylformamide previously supplemented as in Example 1 with 0.7 g of 80% sodium hydride. After stirring for 1 hour 30 minutes at the same temperature, 5 ml of distilled water are slowly added and then the mixture is poured over 200 ml of distilled water and extracted 3 times with a total of 180 ml of chloroform. The organic extracts are pooled, washed with 60 ml of distilled water, dried over anhydrous sodium sulphate and concentrated to dryness under reduced pressure (15 mmHg; 2 kPa) at 60° C. The product obtained (1 g) is chromatographed on 60 g of neutral silica gel. (0.020–0.045 mm) contained in a column 2.9 cm in diameter, eluting under pressure with an ethyl acetate-methanol mixture (85–15 by volume) and collecting 10-ml fractions. Fractions 24 to 56 are pooled and concentrated to dryness under reduced pressure (15 mmHg; 2 kPa) at 40° C. 0.69 g of ethyl 1-[5-(1-imidazolyl)-1-oxo-2-indanyl]imidazole-2-carboxylate is thus obtained [Rf=0.4, thin-layer chromatography on silica gel; solvent: ethyl acetate-methanol (80–20 by volume)].

The 5-(1-imidazolyl)-1-indanone can be prepared as described in European Patent 314 400.

Example 9

1 g of potassium nitrate is added over 10 minutes at a temperature close to 5° C. to a solution of 2.6 g of 5H, 10H-imidazo[1,2-a]indeno[1,2-e]pyrazin-4-one hydrochloride in 20 ml of concentrated sulphuric acid (d=1.83). The mixture is stirred for 30 minutes at the same temperature and for 3 hours at 25° C. and is then poured over 150 ml of ice-cold water. The crystals which appear are separated by filtration, washed with distilled water and then with acetone and dried under reduced pressure (1 mmHg; 0.13 kPa) at 80° C. 2.1 g of 8-nitro-5H, 10H-imidazo[1,2-a]indeno[1,2-e] pyrazin-4-one are thus obtained which decompose without melting above 300° C. [NMR spectrum: (200 MHz; DMSO-$d_6$; δ in ppm): 4.23 (s, 2H; —C$\underline{H}$2— in position 10); 7.68 and from 8.12 (2s broad, 1H each: —$\underline{H}$ of imidazole); 8.07 (dd, J=8.5 Hz, 1H: —$\underline{H}$6); 8.38 (dd, J=8.5 and 1.5 Hz, 1H: —$\underline{H}$7); 8.50 (d, J=1.5 Hz, 1H: —$\underline{H}$9); 12.64 (unresolved complex, 1H: —CON$\underline{H}$—)].

Example 10

0.5 g of 5H, 10H-imidazo[1,2-a]indeno-[1,2-e]pyrazin-4-one hydrochloride is dissolved in 1.9 g of chlorosulphonic acid at 5° C. The solution obtained is stirred for 10 minutes at the same temperature and for 1 hour at 20° C. and is then poured over 50 g of water and ice. The insoluble matter which appears is separated by filtration, successively washed 3 times with a total of 30 ml of distilled water, 3 times with a total of 30 ml of acetone and with 10 ml of ethyl ether and then air dried. The product obtained (0.5 g) is dissolved in 50 ml of a 2N aqueous sodium hydroxide solution and then the mixture is acidified to pH 2 by addition of a 1N aqueous hydrochloric acid solution. The insoluble matter which appears is separated by filtration, successively washed 3 times with a total of 30 ml of distilled water, 3 times with a total of 30 ml of acetone and with 10 ml of ethyl ether and then dried under reduced pressure (1 mmHg; 0.13 kPa) at 50° C. 0.45 g of 4-oxo-5H, 10H-imidazo[1,2-a] indeno-[1,2-e]-pyrazin-8-sulphonic acid is thus obtained which decomposes without melting above 300° C. [NMR spectrum: (300 MHz; DMSO-$d_6$; δ in ppm): 4.10 (s, 2H: —C$\underline{H}$2— in position 10); 7.69 (dd, J=8 and 1 Hz 1H: —$\underline{H}$7); 7.85 (d, J=1 Hz, 1H: —$\underline{H}$9); 7.86 (d, j=8 Hz, 1H: —$\underline{H}$6); 8.11 and 8.36 (2d, J=1 Hz, 1H each: —$\underline{H}$ of imidazole); 13.27 (unresolved complex, 1H: —CON$\underline{H}$—)].

Example 11

A solution of 2.3 g of 3,7-dimethyl-4-oxo-5H, 10H-imidazo[1,2-a]indeno[1,2-e]pyrazinium bromide in 15 g of imidazole is stirred under a nitrogen atmosphere for 20 hours at 160° C., cooled to 100° C. and then poured over 60 g of a mixture of distilled water and ice. The insoluble matter is separated by filtration, washed twice with a total of 10 ml of distilled water and with 5 ml of ethyl ether and then air dried. The product (1.7 g) is chromatographed on 100 g of neutral silica gel (0.020–0.045 mm) contained in a column 3.2 cm in diameter, eluting under pressure with a dichloromethane-methanol mixture (97–7 by volume) and collecting 10-ml fractions. The fractions 35 to 182 are pooled and concentrated to dryness under reduced pressure (15 mmHg; 2 kPa) at 40° C. The product obtained (0.6 g) is dissolved in a boiling mixture of 64 ml of dimethylformamide and 16 ml of distilled water and the solution, supplemented with decolorizing charcoal, is filtered hot, cooled and kept for 16 hours at 5° C. The crystals are separated by filtration, washed with 3 ml of distilled water and with 3 ml of ethanol and then dried under reduced pressure (1 mmHg; 0.13 kPa) at 60° C. 0.3 g of 7-methyl-5H, 10H-imidazo[1,2-a]indeno[1,2-e]pyrazin-4-one is thus obtained which decomposes without melting above 300° C. [NMR spectrum: (200 MHz; DMSO-$d_6$; δ in ppm): 2.40 (s, 3H: Ar—C$\underline{H}$3); 3.98 (s, 2H: —C$\underline{H}$2— in position 10); 7.15 (broad d, J=8 Hz 1H: —$\underline{H}$8); 7.49 (d, J=8 Hz, 1H: —$\underline{H}$9); 7.60 and 7.99 (2s broad, 1H each: —$\underline{H}$ of imidazole); 7.72 (broad s, 1H: —$\underline{H}$6); 12.35 (unresolved complex, 1H: —CON$\underline{H}$—)].

The 3,7-dimethyl-4-oxo-5H, 10H-imidazo[1,2-a]-indeno[1,2-e]pyrazinium bromide can be prepared in the following manner: a solution of 4.75 g of 2-bromo-6-methyl-1-indanone and 2 g of 1-methyl-1H-imidazole-2-carboxamide in 40 ml of anhydrous dimethylformamide is stirred for 16 hours at 115° C. and cooled to 20° C. The crystals are separated by filtration, washed twice with a total of 20 ml of ethyl ether and dried under reduced pressure (15 mmHg; 2 kPa) at 50° C. 2.4 g of 3,7-dimethyl-4-oxo-5H, 10H-imidazo[1,2-a]indeno[1,2-e]-pyrazinium bromide are thus obtained [Rf=0.23, thin-layer chromatography on silica gel, solvent: dichloromethane-methanol (8–2 by volume)].

The 2-bromo-6-methyl-1-indanone can be prepared as described by J. CHAKRAVARTY, Indian J. Chem., 7(3), 215 (1969).

Example 12

A solution of 4.8 g of 3-methyl-4-oxo-5H, 10H-imidazo[1,2-a]indeno[1,2-e]pyrazinium bromide in 30 g of imidazole is heated for 24 hours at 160° C., cooled to 100° C. and then poured over a stirred mixture of 75 g of ice and 75 g of distilled water. The insoluble matter is filtered, washed twice with a total of 20 ml of distilled water and then dried under reduced pressure (10 mmHg; 1.3 kPa) at 50° C. The product thus obtained (4 g) is dissolved in 80 ml of dimethylformamide and the solution, supplemented with 20 g of silica, is concentrated to dryness under reduced pressure (15 mmHg, 2 kPa) at 100° C. The mixture is introduced into a column 4.2 cm in diameter containing 240 g of silica and it is then eluted with a dichloromethane-methanol mixture (97–3 by volume), collecting 60-ml fractions. Fractions 10 to 70 are pooled, supplemented with 1.5 g of decolorizing charcoal, filtered and concentrated to dryness under reduced pressure (15 mmHg; 2 kPa) at 55° C. The product obtained (1.7 g) is dissolved in 350 ml of boiling methanol and the solution, supplemented with 0.1 g of decolorizing charcoal, is filtered hot, concentrated under reduced pressure (15 mmHg; 2 kPa) at 40° C. in order to adjust its volume to about 30 ml and then preserved at 5° C. for 60 hours. The crystals are separated by filtration, washed twice with a total of 20 ml of ice-cold methanol and dried under reduced pressure (1 mmHg; 0.13 kPa) at 60° C. 1.1 g of 5H, 10H-imidazo[1,2-a]— indeno[1,2-e]pyrazin-4-one are thus obtained which decompose without melting at 350° C. [Rf=0.77, thin-layer chromatography on silica gel, solvent: dichloromethane-methanol (8–2 by volume)].

The 3-methyl-4-oxo-5H, 10H-imidazo[1,2-a]-indeno[1,2-e]pyrazinium bromide can be prepared in the following manner: a solution of 5 g of 1-methyl-1H-imidazole-2-carboxamide and 12 g of 85% 2-bromoindanone in 100 ml of anhydrous dimethylformamide is stirred for 28 hours at 115° C. and then cooled to a temperature close to 20° C. The insoluble matter is separated by filtration, washed twice with a total of 20 ml of ice-cold dimethylformamide and dried under reduced pressure (10 mmHg; 1.3 kPa). 4.8 g of 3-methyl-4-oxo-5H, 10H-imidazo[1,2-a]indeno[1,2-e] pyrazinium bromide is thus obtained which is used as it is in subsequent syntheses [NMR spectrum: (200 MHz; DMSO-$d_6$; δ in ppm): 4.13 (s, 2H: —C$\underline{H}$2 in position 10); 4.34 (s, 3H: N$^+$ —C$\underline{H}$3); 7.47 (mt, 2H: $\underline{H}$7 and $\underline{H}$8); 7.68 and 7.96 (2d, J=7.5 Hz, 1H each: $\underline{H}$6 and $\underline{H}$9); 8.32 and 8.45 (2d, J=1 Hz, 1H each: $\underline{H}$ of imidazole); 13.60 (unresolved complex, 1H: N$\underline{H}$)].

The 1-methyl-1H-imidazole-2-carboxamide can be prepared according to the process described by D. D. DAVEY, J. Org. Chem., 52, 4379 (1987).

Example 13

The procedure is carried out as in Example 1 starting with 3.8 g of 1-(5-bromo-1-oxo-2-indanyl)imidazole-2-carboxamide, a total of 420 ml of methanol and 57 ml of a 12N aqueous hydrochloric acid solution. 3 g of 8-bromo-5H, 10H-imidazo[1,2-a]indeno-[2-e]pyrazin-4-one hydrochloride are thus obtained which decompose without melting above 300° C. [NMR spectrum: (300 MHz; DMSO-$d_6$; δ in ppm): 4.12 [s, 2H: —C$\underline{H}$2— in position 10 (observed in DMSO-$d_6$ plus a few drops of CD3COOD-$d_4$)]; 7.68 (dd, J=8 and 2 Hz, 1H: —$\underline{H}$7); 7.90 (broad s, 1H: —$\underline{H}$9); 7.93 (d, j=8 Hz, 1H: —$\underline{H}$6); 8.02 and 8.32 (2d, J=1 Hz, 1H each: —$\underline{H}$ of imidazole); 13.18 (broad s, 1H: —CON$\underline{H}$—)].

The 1-(5-bromo-1-oxo-2— indanyl)imidazole-2-carboxamide can be prepared as in Example 1 for the preparation of 1-(5-fluoro-1-oxo-2— indanyl)imidazole-2-carboxamide but starting with 3.7 g of ethyl 1-(5-bromo-1-oxo-2— indanyl)imidazol e -2-carboxylate and 300 ml of a 5N ammoniacal methanol solution. 3.2 g of 1-(5-bromo-1-oxo-2— indanyl)imidazole-2-carboxamide are thus obtained in the form of a solid which melts at 240° C.

The ethyl 1-(5-bromo-1-oxo-2-indanyl)imidazole-2-carboxylate can be prepared in the following manner: a solution of 9.5 g of ethyl imidazole-2-carboxylate, 9.9 g of 2,5-dibromo-1-indanone and 0.1 g of sodium iodide in 280 ml of ethanol is kept boiling for 16 hours, cooled to 20° C. and dried under reduced pressure (20 mmHg; 2.6 kPa) at 50° C. The product obtained (21 g) is dissolved in 50 ml of dichloromethane and the solution is washed 3 times with a total of 600 ml of distilled water, dried over anhydrous magnesium sulphate and dried under reduced pressure (20 mmHg; 2.6 kPa) at 50° C. The product obtained (12.7 g) is chromatographed on 790 g of neutral silica gel (0.020–0.045 mm) contained in a column 7 cm in diameter, eluting under pressure with a dichloromethane-ethyl acetate mixture (70–30 by volume) and collecting 75-ml fractions. Fractions 70 to 140 are pooled and concentrated to dryness under reduced pressure (15 mmHg; 2 kPa) at 40° C. 3.7 g of ethyl 1-(5-bromo-1-oxo-2-indanyl)imidazole-2-carboxylate are thus obtained which melt at 140° C.

The 2,5-dibromo-1-indanone can be prepared as described in European Patent 346107.

Example 14

420 mg of 1-(4-fluoro-1-oxo-2-indanyl-imidazole-2-carboxamide are dissolved in 20 ml of boiling methanol and the solution, supplemented with 0.2 g of decolorizing charcoal, is filtered hot, concentrated under reduced pressure (15 mmHg; 2 kPa) at 40° C. To the residue thus obtained, there are added 6 ml of 12N hydrochloric acid and the solution is kept at 5° C. for 60 hours. The crystals are separated by filtration and redissolved in 20 ml of boiling methanol. After addition of 20 ml of 6N hydrochloric ether and filtration, 130 mg of 9-fluoro-5H, 10H-imidazo[1,2-a]-indeno[1,2-e]pyrazin-4-one in hydrochloride form which melt at a temperature greater than 260° C. (analysis: % calculated C: 56.23, H: 3.27, Cl: 12.77, F: 6.84, N: 15.13, % found C: 56.20, H: 3.40, Cl: 13.00, F: 5.90, N: 14.40).

The 1-(4-fluoro-1-oxo-2-indanyl)imidazole-2-carboxamide can be obtained in the following manner: 720 mg of ethyl 1-(4-fluoro-1-oxo-2-indanyl)imidazole-2-carboxylate are dissolved in 50 ml of a 3N ammoniacal methanol solution and the solution is kept stirring for 20 hours at a temperature close to 20° C., and then concentrated to dryness under reduced pressure (15 mmHg; 2 kPa) at 40° C. The residue thus obtained is purified by flash chromatography on a silica column, under a nitrogen stream at medium pressure (0.5 bar) with ethyl acetate as eluent. 420 mg of 1-(4-fluoro-1-oxo-2-indanyl)imidazole-2-carboxamide are thus obtained which melt at 159° C.

The ethyl 1-(4-fluoro-1-oxo-2-indanyl)-imidazole-2-carboxylate can be obtained in the following manner: the solution of 5.3 g of ethyl imidazole-2-carboxylate in 20 ml of anhydrous dimethylformamide is added dropwise over 30 minutes at a temperature close to 20° C. to a suspension of 2.43 g of 50% sodium hydride in 60 ml of anhydrous dimethylformamide kept under a nitrogen atmosphere. After stirring for 15 minutes, a solution of 9.26 g of 2-bromo-4-fluoro-1-indanone in 25 ml of anhydrous dimethylformamide is added dropwise over 30 minutes at a temperature close to 20° C. The mixture is stirred for 18 hours, and then after slowly adding 30 ml of water, poured into 200 ml of distilled water and extracted four times with 100 ml of dichloromethane. The organic phases are pooled, washed with 600 ml of distilled water, dried over anhydrous sodium sulphate and concentrated to dryness under reduced pressure (15 mmHg; 2 kPa) at 45° C. The residue thus obtained is purified by flash chromatography on a silica column, under a nitrogen stream at medium pressure (0.5 bar) with ethyl acetate as eluent. 1.2 g of ethyl 1-(4-fluoro-1-oxo-2-indanyl) imidazole-2-carboxylate are thus obtained which melt at 145° C.

The 2-bromo-4-fluoro-1-indanone can be obtained in the following manner: to a solution of 8 g of 4-fluoro-1-indanone in 400 ml of dioxane, are added 31.3 g of copper bromide. The solution is then heated to a temperature close to 100° C. for 4 hours. The reaction medium is then filtered on celite and then concentrated to dryness under reduced pressure (15 mmHg; 2 kPa) at 40° C. 13.23 g of 2-bromo-4-fluoro-1-indanone is thus obtained which is used as it is in subsequent syntheses.

The 4-fluoro-1-indanone can be prepared as described by M. OLIVIER and E. MARECHAL, Bull. Soc. Chim. Fr., (11), 3042 (1973).

Example 15

The procedure is carried out as in Example 14 but starting with 0.26 g of 1-(6,7-dichloro-1-oxo-2-indanyl)imidazole-2-carboxamide, 80 ml of methanol and 20 ml of hydrochloric acid (12N). 97 mg of 6,7-dichloro-5H, 10H-imidazo[1,2-a]indeno[1,2-e]pyrazin-4-one are thus obtained in hydrochloride form which melt at a temperature greater than 260° C. (analysis: % calculated C: 49.35, H: 2.44, Cl: 29.88, N: 13.28, % found C: 49.40, H: 2.10, Cl: 29.90, N: 13.10).

The 1-(6,7-dichloro-1-oxo-2-indanyl)imidazole-2-carboxamide can be prepared as in Example 14 for the preparation of 1-(4-fluoro-1-oxo-2-indanyl)imidazole-2-carboxamide but starting with 1 g of ethyl 1-(6,7-dichloro-1-oxo-2-indanyl)imidazole-2-carboxylate and 56 ml of a 3N ammoniacal methanol solution. 270 mg of 1-(6,7-dichloro-1-oxo-2-indanyl)imidazole-2-carboxamide are thus obtained which melt at 270° C.

The ethyl 1-(6,7-dichloro-1-oxo-2-indanyl)-imidazole-2-carboxylate can be prepared as in Example 14 for the preparation of ethyl 1-(4-fluoro-1-oxo-2-indanyl)imidazole-2-carboxylate but starting with 2.5 g of ethyl imidazole-2-carboxylate, 0.65 g of 80% sodium hydride, 6.06 g of 2-bromo-6,7-dichloro-1-indanone and a total of 36 ml of anhydrous dimethylformamide. After purification by silica column chromatography with ethyl acetate as eluent, 1 g of ethyl 1-(6,7-dichloro-1-oxo-2-indanyl)imidazole-2-carboxylate is obtained which melts at 90° C.

The 2-bromo-6,7-dichloro-1-indanone is prepared as in Example 14 for the preparation of 2-bromo-4-fluoro-1-indanone but starting with 7.42 g of 6,7-dichloro-1-indanone, 21.8 g of copper bromide and 240 ml of dioxane. After purification by silica column chromatography with an ethyl acetate-cyclohexane mixture (10–90 by volume) as eluent, 6.79 g of 2-bromo-6,7-dichloro-1-indanone are obtained which melt at 103° C.

The 6,7-dichloro-1-indanone can be prepared in the following manner: 58.8 g of 3-(3,4-dichlorophenyl)propionic acid and 315 ml of thionyl chloride are refluxed for 45 minutes. After removing, by distillation, the excess thionyl chloride, 1200 ml of anhydrous dichloromethane and 47 g of aluminium chloride are added. The reaction medium is refluxed for 6 hours, cooled and 1366 ml of a 1N aqueous hydrochloric acid solution are added. After decantation, the organic phase is washed with 1700 ml of an aqueous potassium hydroxide solution (5%) and 600 ml of distilled water, dried over anhydrous magnesium sulphate and concentrated to dryness under reduced pressure (15 mmHg; 2 kPa) at 40° C. The residue thus obtained is purified by flash chromatography on a silica column under a nitrogen stream at medium pressure (0.5 bar) with an ethyl acetate-cyclohexane mixture (20–80) as eluent. 7.42 g of 6,7-dichloro-1-indanone which melt at 129° C. and 21.8 g of 5,6-dichloro-1-indanone which melt at 150° C. are thus obtained.

The 3-(3,4-dichlorophenyl)propionic acid can be prepared in the following manner: to a solution of 69.86 g of 3,4-dichlorocinnamic acid, 1750 ml of methanol and 21 g of hexahydrated nickel chloride, there are added over 75 minutes, while the temperature is kept close to 20° C., 57.75 g of sodium borohydride. After stirring for one hour at a temperature close to 20° C., the solution is filtered and then concentrated to dryness under reduced pressure (15 mmHg; 2 kPa) at 40° C. The residue thus obtained is dissolved in 875 ml of an aqueous potassium hydroxide solution (5%) and extracted with 1000 ml of ethyl ether. The aqueous phase is acidified with 945 ml of a 2N aqueous hydrochloric acid solution and then extracted with two times 1000 ml of ethyl ether. The organic phase is dried over anhydrous magnesium sulphate, concentrated to dryness under reduced pressure (15 mmHg; 2 kPa) at 40° C. and 58.8 g of 3-(3,4-dichlorophenyl)propionic acid are obtained which melt at 90° C.

Example 16

The procedure is carried out as in Example 14 but starting with 0.11 g of 1-(7,8-dichloro-1-oxo-2-indanyl)imidazole-2-carboxamide, 10 ml of methanol and 35 ml of hydrochloric acid (12N). 30 mg of 7,8-dichloro-5H, 10H-imidazo[1,2-a]indeno[1,2-e]pyrazin- 4-one are thus obtained in hydrochloride form which melt at a temperature greater than 260° C. [infrared spectrum (KBr)characteristic bands in cm$^{-1}$: 3425, 3200 to 2125, 2000, 3125, 3140, 3020, 1710 and shoulder at 1695, 1645, 1550, 1500, 1450, 1385, 1105, 780 and 675].

The 1-(7,8-dichloro-1-oxo-2-indanyl)imidazole-2-carboxamide is prepared as in Example 14 for the preparation of 1-(4-fluoro-1-oxo-2-indanyl)imidazole-2-carboxamide but starting with 0.18 g of ethyl 1-(7,8-dichloro-1-oxo-2-indanyl)imidazole-2-carboxylate and 10 ml of a 3N ammoniacal methanol solution. 0.13 mg of 1-(7,8-dichloro-1-oxo-2-indanyl)imidazole-2-carboxamide is thus obtained which melts at 264° C.

The ethyl 1-(7,8-dichloro-1-oxo-2-indanyl)imidazole-2-carboxylate is prepared as in Example 14 for the preparation of ethyl 1-(4-fluoro-1-oxo-2-indanyl)imidazole-2-carboxylate but starting with 1.66 g of ethyl imidazole-2-carboxylate, 0.47 g of 80% sodium hydride, 4 g of 2-bromo-5,6-dichloro-1-indanone and a total of 24 ml of anhydrous dimethylformamide. After purifying by silica column chromatography with an ethyl acetate-dichloromethane mixture (40–60 by volume) as eluent, 0.2 g of ethyl 1-(7,8-dichloro-1-oxo-2-indanyl)imidazole-2-carboxylate is obtained which melts at 103° C.

The 2-bromo-5,6-dichloro-1-indanone is prepared as in Example 14 for the preparation of 2-bromo-4-fluoro-1-indanone but starting with 5.48 g of 5,6-dichloro-1-indanone, 16.1 g of copper bromide and 175 ml of dioxane. After purifying by silica column chromatography with an ethyl acetate-cyclohexane mixture (10–90 by volume) as eluent, 4.07 g of 2-bromo-5,6-dichloro-1-indanone are obtained which melt at 85° C.

Example 17

The procedure is carried out as in Example 14 but starting with 0.72 g of 1-(8,9-dichloro-1-oxo-2-indanyl)imidazole-2-carboxamide, 220 ml of methanol and 55 ml of hydrochloric acid (12N). 0.57 g of 8,9-dichloro-5H, 10H-imidazo[1,2-a]indeno[1,2-e]pyrazin-4-one is thus obtained in hydrochloride form which melts at a temperature greater than 260° C. (analysis: % calculated C: 53.45, H: 2.42, Cl: 24.27, N: 14.38, O: 5.4, % found C: 53.50, H: 2.50, Cl: 23.50, N: 14.40, O: 5.8).

The 1-(8,9-dichloro-1-oxo-2-indanyl)imidazole-2-carboxamide can be prepared as in Example 14 for the preparation of 1-(4-fluoro-1-oxo-2-indanyl)imidazole-2-carboxamide but starting with 1.77 g of ethyl 1-(8,9-dichloro-1-oxo-2-indanyl)imidazole-2-carboxylate and 95 ml of a 3N ammoniacal methanol solution. 0.66 g of 1-(8,9-dichloro-1-oxo-2-indanyl)imidazole-2-carboxamide is thus obtained which melts at 202° C.

The ethyl 1-(8,9-dichloro-1-oxo-2-indanyl)imidazole-2-carboxylate can be prepared in the following manner: a mixture of 4.2 g of ethyl imidazole-2-carboxylate and 4.2 g of 2-bromo-4,5-dichloro-1-indanone is heated at 130° C. for 20 minutes, cooled to 20° C. and dissolved in 90 ml of dichloromethane. The solution is washed with 35 ml of water. The organic phase is washed with 45 ml of a saturated aqueous sodium bicarbonate solution, 135 ml of distilled water, dried over anhydrous sodium sulphate and concentrated to dryness under reduced pressure (15 mmHg; 2 kPa) at 40° C. The residue thus obtained is purified by flash chromatography on a silica column with an ethyl acetate-cyclohexane mixture (60–40 by volume) as eluent. 1.28 g of ethyl 1-(8,9-dichloro-1-oxo-2-indanyl)imidazole-2-carboxylate are thus obtained which melt at 158° C.

The 2-bromo-4,5-dichloro-1-indanone can be prepared as in Example 14 for the preparation of 2-bromo-4-fluoro-1-indanone but starting with 12.67 g of 4,5-dichloro-1-indanone, 37.3 g of copper bromide and 400 ml of dioxane. 16.79 g of 2-bromo-6,7-dichloro-1-indanone are thus obtained which melt at 131° C.

The 4,5-dichloro-1-indanone is prepared as in Example 15 for the preparation of 6,7-dichloro-1-indanone but star6ing with 26 g of 3-(2,3-dichlorophenyl)propionic acid, 138 ml of thionyl chloride, 550 ml of anhydrous dichloromethane and 20.5 g of aluminium chloride. After recrystallization from 100 ml of boiling ethanol, 12.67 g of 4,5-dichloro-1-indanone are thus obtained which melt at 78° C.

The 3-(2,3-dichlorophenyl)propionic acid can be prepared as in Example 15 for the preparation of 3-(3,4-dichlorophenyl)propionic acid but starting with 33 g of 2,3-dichlorocinnamic acid, 800 ml of methanol and 9.9 g of hexahydrated nickel chloride and 27.22 g of sodium borohydride. 26.33 g of 3-(2,3-dichlorophenyl)propionic acid are obtained which melt at 100° C.

Example 18

The procedure is carried out as in Example 14 but starting with 1.27 g of 1-(7,9-dichloro-1-oxo-2-indanyl)imidazole-2-carboxamide, 390 ml of methanol and 96 ml of hydrochloric acid (12N). 1.44 g of 7,9-dichloro-5H, 10H-imidazo[1,2-a]indeno[1,2-e]pyrazin-4-one are thus obtained in hydrochloride form which melt at a temperature greater than 260° C. (analysis: % calculated C: 47.52, H: 2.45, Cl: 32.37, N: 12.79, O: 4.87, % found C: 47.20, H: 2.30, Cl: 32.10, N: 12.70, O: 4.80).

The 1-(7,9-dichloro-1-oxo-2-indanyl)imidazole-2-carboxamide can be prepared as in Example 14 for the preparation of 1-(4-fluoro-1-oxo-2-indanyl)imidazole-2-carboxamide but starting with 2.60 g of ethyl 1-(7,9-dichloro-1-oxo-2-indanyl)imidazole-2-carboxylate and 145 ml of a 3N ammoniacal methanol solution 1.30 g of 1-(7,9-dichloro-1-oxo-2-indanyl)imidazole-2-carboxamide are thus obtained which melt at a temperature greater than 260° C. (Rf=0.49, thin-layer chromatography on silica gel, solvent: ethyl acetate).

The ethyl 1-(7,9-dichloro-1-oxo-2-indanyl)-imidazole-2-carboxylate can be prepared in the following manner: a mixture of 7.25 g of ethyl imidazole-2-carboxylate and 7.25 g of 2-bromo-4,6-dichloro-1-indanone is heated at 130° C. for 30 minutes, cooled to 20° C. and dissolved in 100 ml of dichloromethane. The solution is washed with 200 ml of water. The organic phase is washed with 200 ml of a saturated aqueous sodium bicarbonate solution, 240 ml of distilled water, dried over anhydrous sodium sulphate and concentrated to dryness under reduced pressure (15 mmHg; 2 kPa) at 40° C. The residue thus obtained is purified by flash chromatography on a silica column with an ethyl acetate-cyclohexane mixture (80–20 by volume) as eluent. 2.90 g of ethyl 1-(7,9-dichloro-1-oxo-2-indanyl)imidazole-2-carboxylate are thus obtained which melt at 127° C.

The 2-bromo-4,6-dichloro-1-indanone is prepared as in Example 14 for the preparation of 2-bromo-4-fluoro-1-indanone but starting with 21.6 g of 4,6-dichloro-1-indanone, 63.56 g of copper bromide and 690 ml of dioxane. 14.5 g of 2-bromo-4,6-dichloro- 1-indanone are obtained which melt at 80° C.

The 4,6-dichloro-1-indanone can be prepared as in Example 15 for the preparation of 6,7-dichloro-1-indanone but starting with 53 g of 3-(2,4-dichlorophenyl)propionic acid, 284 ml of thionyl chloride, 1130 ml of anhydride dichloromethane and 42.16 g of aluminium chloride. After recrystallization from 150 ml of boiling ethanol, 21.62 g of 4,6-dichloro-1-indanone are obtained which melt at 120° C.

The 3-(2,4-dichlorophenyl)propionic acid can be prepared as in Example 15 for the preparation of 3-(3,4-dichlorophenyl)propionic acid but starting with 66 g of 2,4-dichlorocinnamic acid, 1600 ml of methanol, 19.8 g of hexahydrated nickel chloride and 54.44 g of sodium borohydride. 53.44 g of 3-(2,4-dichlorophenyl)-propionic acid are thus obtained which melt at 83° C.

Example 19

1 g of 9-bromo-5H, 10H-imidazo[1,2-a]indeno-[1,2-e]pyrazin-4-one is added to 6 ml of concentrated sulphuric acid (20N) at a temperature close to 0° C. 0.3 g of potassium nitrate is then added in two portions to this solution while maintaining the temperature between 0° and 5° C. The reaction medium is stirred for 18 hours at 20° C., then poured into 50 ml of ice-cold water. The insoluble matter is filtered, washed with 50 ml of ethyl acetate and dried under reduced pressure (15 mmHg; 2 kPa) at 50° C. 0.77 g of 8-nitro-9-bromo-5H, 10H-imidazo[1,2-a]indeno[1,2-e]-pyrazin-4-one is thus obtained which melts above 260° C. (analysis: % calculated C: 44.98, H: 2.03, Br: 23.02, N: 16.14, % found C: 45.40, H: 2.20, Br: 21.30, N: 15.70).

The 9-bromo-5H, 10H-imidazo[1,2-a]indeno-[1,2-e]pyrazin-4-one can be prepared in the following manner: 4.6 g of 1-(4-bromo-1-oxo-2-indanyl)imidazole-2-carboxamide are dissolved in 350 ml of boiling methanol and the solution, supplemented with 0.2 g of decolorizing charcoal, is filtered hot, concentrated under reduced pressure (15 mmHg; 2 kPa) at 40° C. To the residue thus obtained, there are added 150 ml of 12N hydrochloric acid and the solution is preserved at 5° C. for 18 hours. The crystals are separated by filtration and redissolved in 150 ml of boiling methanol. After addition of 170 ml of 12N hydrochloric acid, the medium is heated at 80° C. for one hour. After filtration, 3.45 g of 9-bromo-5H, 10H-imidazo[1,2-a]indeno [1,2-e]pyrazin-4-one are obtained in hydrochloride form which melt at a temperature greater than 260° C. (analysis: % calculated C: 46.11, H: 2.68, Br: 23.60, Cl: 10.47, N: 12.41, O: 4.73, % found C: 46.20, H: 2.60, Br: 23.8, Cl: 9.90, N: 12.30, O: 4.80).

The 1-(4-bromo-1-oxo-2-indanyl)imidazole-2-carboxamide can be obtained in the following manner: a solution of 3.5 g of ethyl 1-(4-bromo-1-oxo-2-indanyl)imidazole-2-carboxylate in 20 ml of methanol is maintained saturated for one hour, with boiling, with a stream of ammonia gas. The reaction medium is then concentrated to dryness under reduced pressure (15 mmHg; 2 kPa) at 40° C. 3.10 g of 1-(4-bromo-1-oxo-2-indanyl)imidazole-2-carboxamide are thus obtained which melt at 212° C.

The ethyl 1-(4-bromo-1-oxo-2-indanyl)-imidazole-2-carboxylate can be obtained in the following manner: a mixture of 9.28 g of ethyl imidazole-2-carboxylate and 8.50 g of 2,4-dibromo-1-indanone is heated at 130° C. for 20 minutes, cooled to 20° C. and dissolved in 50 ml of dichloromethane. The solution is washed twice with 100 ml of water. The organic phase is washed with 50 ml of a 0.1N aqueous sodium hydroxide solution, 300 ml of distilled water, dried over anhydrous sodium sulphate and concentrated to dryness under reduced pressure (15 mmHg; 2 kPa) at 40° C. The residue thus obtained is purified by flash chromatography on a silica column, under a nitrogen stream at medium pressure (0.5 bar) with ethyl acetate as eluent. 3.5 g of ethyl 1-(4-bromo-1-oxo-2-indanyl)-imidazole-2-carboxylate are thus obtained which melt at 157° C.

The 2,4-dibromo-1-indanone can be obtained in the following manner: a solution of 24 g of 4-bromo-1-indanone and 120 ml of chloroform is cooled to 5° C. A solution of 18.2 g of bromine and 20 ml of chloroform is then added dropwise over two hours at a temperature of between 0° and 5° C. stirring leaving the reaction medium stirring for one hour while maintaining the introduction temperature, the solution is allowed to return to room temperature and it is further stirred for one hour. The reaction medium is then concentrated to dryness under reduced pressure (15 mmHg; 2 kPa) at 40° C. The residue thus obtained is purified by flash chromatography on a silica column, under a nitrogen stream at medium pressure (0.5 bar) with an ethyl acetate-cyclohexane mixture (10–90 by volume) as eluent. 13.63 g of 2,4-dibromo-1-indanone are thus obtained which melt at 80° C.

The 4-bromo-1-indanone can be prepared as described by F. G. HOLLIMAN, F. G. MANNE and D. A. THORNTON, J. Chem. Soc., 9 (1960).

Example 20

6.3 g of ethyl 1-(5-methoxy-1-oxo-2-indanyl)-imidazole-2-carboxylate are dissolved in a 4N ammonium acetate solution in glacial acetic acid. After refluxing for 12 hours, the mixture is cooled to a temperature close to 20° C. and filtered. The solid obtained is washed with water until a neutral pH is obtained and with 50 ml of acetone, then it is recrystallized in a hot state from 75 ml of dimethylformamide. The crystals formed are separated by filtration and successively rinsed with 50 ml of water and 50 ml of acetone. 3.3 g of 5H, 10H- 8-methoxy-imidazo-[1,2-a]indeno[1,2-e]pyrazin-4-one are thus obtained in the form of a beige solid which melts above 260° C. [NMR spectrum: (200 MHz; DMSO-d$_6$; δ in ppm): 3.82 (s, 3H: —OC—H3); 3.98 (s, 2H: —CH2— in position 10); 6.98 (dd, J=8 and 1.5 Hz, 1H: —H7); 7.22 (d, J=1.5 Hz, 1H: —H9); 7.56 and 7.97 (2s, 1H each: —H of imidazole) 7.78 (d, J=8 Hz, 1H: —H6); 12.30 (broad s, 1H: —CO—NH)].

The ethyl 1-(5-methoxy-1-oxo-2-indanyl)-imidazole-2-carboxylate can be prepared in the following manner: a mixture of 13.9 g of 2-bromo-5-methoxy-1-indanone and 16.2 g of 2-ethoxycarbonyl-imidazole in 300 ml of toluene is refluxed for 9 hours. The toluene is then evaporated under reduced pressure and the residue is taken up in dichloromethane and water. The organic phase is extracted with dichloromethane and washed with water. After the usual treatment, the crude product is purified by two successive silica column chromatographies with mixtures of dichloromethane and ethyl acetate (70/30 by volume) and dichloromethane and methanol (98/2 by volume) respectively. 7.5 g of ethyl 1-(5-methoxy-1-oxo-2-indanyl)imidazole-1-carboxylate are thus obtained (Rf=0.38, thin-layer chromatography on silica gel, eluent: dichloromethane-ethyl acetate (70–30 by volume)).

The 2-bromo-5-methoxy-1-indanone can be synthesized as described by D. MUXHOPADHYA, D. N. CHAUDHURY, J. Indian Chem. Soc., 47(5), 450 (1970).

Example 21

A mixture of 9.7 g of 5H, 10H-8-nitro-imidazo[1,2-a]indeno[1,2-e]pyrazin-4-one, 370 ml of 0.1N aqueous sodium hydroxide and 0.3 g of 10% palladized carbon is hydrogenated at a temperature close to 20° C. under a pressure of 1.2 bar for 23 hours. The suspension is acidified with 80 ml of 1N hydrochloric acid, then it is filtered. The solid obtained is taken up in 600 ml of boiling water. The mixture is supplemented with animal charcoal and filtered hot on celite. The filtrate crystallizes after cooling on an ice bath. The crystals are separated by filtration and washed twice with 50 ml of ethyl ether. 4.7 g of 5H, 10H-8-amino-imidazo[1,2-a]indeno[1,2-e]pyrazin-4-one monohydrochloride are thus obtained in the form of a beige solid which melts above 260° C. [NMR spectrum: (300 MHz; DMSO-$d_6$; δ ppm): 4.02 (s, 2H: —C—H2— in position 10); 7.00 (broad d, J=8 Hz, 1H: —H7); 7.20 (broad s, 1H: —H9); 7.74 (d, J=8 Hz, 1H: —H6); 7.77 and 8.07 (2s broad, 1H each: —H of imidazole); 12.65 (unresolved complex, 1H: —CO—NH—)].

Example 22

1.7 g of triethylamine and 1.95 g of phenyl isocyanate are successively added to a suspension of 1.5 g of 5H, 10H-8-amino-imidazo[1,2-a]indeno[1,2-e]pyrazin-4-one monohydrochloride in 50 ml of dimethyl sulphoxide. The mixture is stirred at a temperature close to 20° C. for 15 hours, then is poured into 150 ml of ice-cold water. The precipitate formed is separated by filtration and crystallized in a hot state from 20 ml of dimethylformamide. The crystals are filtered and washed twice with 50 ml of ethyl ether. 1.4 g of 5H, 10H-8-(3-phenylureido)-imidazo[1,2-a]indeno[1,2-e]pyrazin-4-one are thus obtained in the form of a pink beige solid which melts above 260° C. [NMR spectrum: (200 MHz; DMSO-$d_6$; δ in ppm): 4.01 (broad s, 2H: —CH2— in position 10); 7.01 (broad t, J=7.5 Hz, 1H: aromatic —H in the para position of —NH—CO—NH—); 7.32 (broad t, J=7.5 Hz, 2H: aromatic —H in the meta position of —NH—CO—NH—); 7.38 (dd, J=8 and 1 Hz, 1H: —H7); 7.50 (broad d, J=7.5 Hz, 2H: aromatic —H in the ortho position of —NH—CO—NH—); 7.58 and 7.95 (2s broad, 1H each: —H of imidazole); 7.77 (d, J=8 Hz, 1H: —H6); 7.88 (d, J=1 Hz, 1H: —H9); 8.77 and 8.86 (2s, 1H each: —NH—CO—NH—); 12.35 (broad s, 1H: —CO—NH—)].

Example 23

To a suspension of 1.5 g of 5H, 10H—8-amino-imidazo[1,2-a]indeno[1,2-e]pyrazin-4-one monohydrochloride in 50 ml of dimethylformamide are added 1.6 g of triethylamine, then 1 g of acetic anhydride. After refluxing for 6 hours, the mixture is cooled and poured into 200 ml of water. The precipitate formed is filtered and crystallized in a hot state from 20 ml of dimethylformamide. The crystals are separated by filtration and washed twice with 50 ml of ethyl ether. 1.4 g of 5H, 10H-8-acetamido-imidazo [1,2-a]indeno[1,2-e]pyrazin-4-one are thus obtained in the form of a pink beige solid which melts above 260° C. [NMR spectrum: (300 MHz; DMSO-$d_6$; d in ppm): 2.10 (s, 3H: —NH—CO—CH3); 4.01 (s, 2H: —CH2— in position 10); 7.52 (dd, J=8 and 1 Hz, 1H: —H7); 7.57 and from 7.90 to 7.95 (s and mt respectively, 1H each: —H of imidazole); 7.75 (d, J=8 Hz, 1H: —H6); from 7.90 to 7.95 (mt, 1H: —H9); 10.03 (broad s, 1H: —N—H—CO—CH3); 12.35 (broad s, 1H: —CO—NH—)].

Example 24

To a mixture of 1.5 g of 5H, 10H—8-amino-imidazo[1,2-a]indeno[1,2-e]pyrazin-4-one monohydrochloride and 1.6 g of triethylamine is added dropwise 1.3 g of methylsulphonyl chloride. The reaction medium is kept stirring for 4 hours at a temperature close to 20° C., and it is then filtered. The resulting solid is washed with 80 ml of water and with 30 ml of hot dimethylformamide. It is then dissolved in 4 ml of boiling water and it precipitates by adding 10 ml of dimethylformmaide. After filtration, 192 mg of 5H, 10H-8-dimethylaminomethyleneamino -imidazo [1,2-a]indeno [1,2-e]pyrazin-4-one monohydrochloride are obtained in the form of a pink solid which melts above 260° C. [NMR spectrum: (250 MHz; DMSO-$d_6$; at a temperature of 343° K.; δ a in ppm): 3.40 [unresolved complex, 6H: —N(CH3)2]; 4.10 (s, 2H: —C—H2— in position 10); 7.55 (dd, J=8 and 1.5 Hz, 1H: —H7); 7.58 and 7.94 (2d, J=1 Hz, 1H each: —H— of imidazole); 7.76 (d, J=1.5 Hz, 1H: H9); 7.92 (d, J=8 Hz, 1H: H6); 8.75 (s, 1H: =N—CH—); 11.60 [unresolved complex, 1H: —N+H(CH3)2Cl-]; 12.22 (unresolved complex, 1H: —CO—NH—)].

Example 25

To a solution of 1.5 g of ethyl 1-(6;fluoro-1-oxo-2-indanyl)imidazole-2-carboxylate in solution in 50 ml of acetic acid, are gradually added 46.7 g of ammonium acetate. The reaction medium is refluxed for 30 min and then cooled to a temperature close to 20° C. The precipitate formed is filtered, washed with water and then with isopropyl ether. 0.7 g of 7-fluoro-5H, 10H-imidazo[1,2-a]indeno [1,2-e]pyrazin-4-one is thus obtained in the form of a beige solid which melts at a temperature greater than 260° C. [$^1$H NMR (DMSO, 200 MHz), δ ppm: 4.00 (broad doublet, 2H: 10—CH₂), 7.14 (split triplet, J=8.5 Hz and 2.5 Hz, 1H: 8—ArH), 7.60 (doublet of doublet, J=8.5 Hz and 5 Hz, 1H: 9—ArH and broad doublet, J=1 Hz, 1H: H-imidazole), 7.70 (doublet of doublet, J=8.5 Hz and 2.5 Hz, 1H: 5—ArH), 8.00 (doublet, J=1 Hz, 1H: H-imidazole), 12.35 (unresolved complex, 1H, NH)].

The ethyl 1-(6-fluoro-1-oxo-2-indanyl)imidazole-2-carboxylate can be prepared in the following manner: 12.8 g of ethyl imidazole-2-carboxylate and 10.1 g of 2-bromo-6-fluoroindanone are heated at 130° C. for 20 minutes. After cooling to a temperature close to 20° C., the mixture is taken up in 100 ml of dichloromethane, washed twice with 30 ml of 0.1N sodium hydroxide and then 3 times with 40 ml of distilled water. After drying the organic phase over magnesium sulphate, it is treated with decolorizing charcoal and concentrated to dryness under reduced pressure (15 mmHg; 2 kPa). The crude product thus obtained (10.6 g) is purified by flash chromatography on a silica column using a mixture of dichloromethane and methanol (98/2 by volume) as eluent. 4.8 g of the expected product are obtained in the form of a beige meringue (Rf=0.19, thin-layer chromatography on silica gel, eluent: dichloromethane-ethyl acetate (70–30 by volume)).

The 2-bromo-6-fluoroindanone can be prepared in the following manner: a solution of 6.4 g of bromine in 30 ml of acetic acid is added dropwise over 25 min at 20° C. to a solution of 12 g of 6-fluoroindanone and 0.05 ml of a 47% aqueous hydrobromic acid solution in 100 ml of acetic acid. After stirring for 5 hours, the mixture is poured over crushed ice. The precipitate formed is filtered, washed with distilled water and then with petroleum ether. 10.1 g of the expected product are thus obtained in the form of a beige solid which melts at 98° C.

The 6-fluoroindanone can be obtained according to the method described by R. Seka and W. Kellermann, Chem. Ber. 75B, 1730 (1942).

Example 26

0.76 g of 1-(1-oxo-2-indanyl)imidazole-2-carboxamide and 3 ml of a 10N aqueous hydrochloric acid solution are stirred at a temperature close to 20° C. for 10 minutes. The heterogeneous reaction medium is diluted with 27 ml of water and heated to the reflux temperature. 200 ml of a 1N aqueous hydrochloric acid solution are then added under reflux until there is complete dissolution of the insoluble matter. After cooling to a temperature close to 20° C. and precipitation, 5H, 10H-imidazo[1,2-a]indeno[1,2-e]pyrazin-4-one hydrochloride is obtained which decomposes without melting at 350° C. [infrared spectrum (KBr), characteristic bands in cm$^{-1}$: 3550; 3250; 3200; 3140; 3125; 3060; 3020; 3000; 2400; 1705; 1645; 1555; 1505; 1460; 1385; 765 and 725].

The 1-(1-oxo-2-indanyl)imidazole-2-carboxamide can be prepared in the following manner: 1.35 g of ethyl 1-(1-oxo-2-indanyl)imidazole-2-carboxylate dissolved in 15 ml of methanol are introduced into 25 ml of a 2.5N ammoniacal methanol solution and the solution is preserved for 20 hours at a temperature close to 20° C. and then concentrated to dryness under reduced pressure (15 mm of Hg; 2 kPa) at 40° C. The product obtained is suspended in 30 ml of isopropyl ether, filtered, washed twice with a total of 20 ml of isopropyl ether and then dried under reduced pressure (15 mm of Hg; 2 kPa) at a temperature close to 20° C. 1.2 g of 1-(1-oxo-2-indanyl)imidazole-2-carboxamide are thus obtained in the form of a solid which melts at 183° C.

The ethyl 1-(1-oxo-2-indanyl)imidazole-2-carboxylate can be prepared in the following manner: to a suspension of 0.4 g of 80% sodium hydride in 5 ml of anhydrous dimethylformamide kept under a nitrogen atmosphere, is added dropwise over 10 minutes at a temperature of between 20 and 25° C. a solution of 1.4 g of ethyl imidazole-2-carboxylate in 15 ml of dimethylformamide. After stirring for 15 minutes, there is added dropwise over 10 minutes a solution of 3 g of 2-bromo-1-indanone in 20 ml of dimethylformamide. The mixture is stirred for 1 hour then, after slowly adding 10 ml of water, poured over 400 ml of distilled water and extracted 3 times with a total of 300 ml of chloroform. The organic extracts are pooled, washed with 100 ml of distilled water, dried over anhydrous sodium sulphate and concentrated to dryness under reduced pressure (15 mm of Hg, 2 kPa) at 35° C. The product obtained (3.55 g) is chromatographed on 215 g of neutral silica gel (0.020-0.045 mm) contained in a column 4.1 cm in diameter, eluting under pressure with a dichloromethane-ethyl acetate mixture (60-40 by volume) and collecting 90-ml fractions. Fractions 16 to 25 are pooled, concentrated to dryness under reduced pressure (15 mm of Hg, 2 kPa) at 35° C. 1.89 g of ethyl 1-(1-oxo-2-indanyl)imidazole-2-carboxylate are thus obtained in the form of a solid which melts at 116° C.

The medicinal products according to the invention consist of a compound of formula (1) or a salt of such a compound, in the pure state or in the form of a composition in which it is combined with any other pharmaceutically compatible product, which may be inert or physiologically active. The medicinal products according to the invention may be used orally, parenterally, rectally or topically.

Tablets, pills, powders (gelatine capsules, cachets) or granules can be used as solid compositions for oral administration. In these compositions, the active ingredient according to the invention is mixed with one or more inert diluents such as starch, cellulose, sucrose, lactose or silica, under an argon stream. These compositions may also contain substances other than diluents, for example one or more lubricant such as magnesium stearate or talc, a colouring, a coating (sugar-coated tablets) or a glaze.

Pharmaceutically acceptable solutions, suspensions, emulsions, syrups and elixirs, containing inert diluents such as water, ethanol, glycerol, vegetable oils or paraffin oil, can be used as liquid compositions for oral administration. These compositions may contain substances other than diluents, for example wetting, sweetening, thickening, flavoring or stabilizing products.

Sterile compositions for parenteral administration may be, preferably, aqueous or nonaqueous solutions, suspensions or emulsions. Water, propylene glycol, a polyethylene glycol, vegetable oils, in particular olive oil, injectable organic esters, for example ethyl oleate or other appropriate organic solvents may be used as solvent or vehicle. These compositions may also contain adjuvants, in particular wetting, isotonizing, emulsifying, dispersing and stabilizing agents. The sterilization can be performed in several ways, for example by asepticizing filtration by incorporating into the composition sterilizing agents, by irradiation or by heating. They can also be prepared in the form of sterile solid compositions which can be dissolved at the time of use in sterile water or any other injectable sterile medium.

Compositions for rectal administration are suppositories or rectal capsules which contain, in addition to the active product, excipients such as cocoa butter, semisynthetic glycerides or polyethylene glycols.

Compositions for topical administration may be for example cremes, lotions, collyria, collutories, nasal drops or sprays.

In human therapy, the compounds according to the invention are particularly useful for the treatment and/or prevention of conditions which require the administration of a AMPA receptor antagonist or of an NMDA receptor antagonist. These compounds are especially useful for the treatment or prevention of all ischaemias and in particular cerebral ischaemia, the effects due to an anoxia, the progression of neurodegenerative diseases, of HUNTINGTON'S chorea, of ALZHEIMER's disease, of amyotrophic lateral sclerosis, of olivopontocerebellar atrophy, and of PARKINSON's disease, against epileptogenic and/or convulsive manifestations, or for the treatment of cerebral or spinal traumas, of anxiety, of depression, of schizophrenia, as analgesics, antianoretics, antiemetics, antimigraines and for the treatment of poisoning by neurotoxins or other substances which are NMDA receptor agonists, as well as neurological disorders associated with viral diseases such as AIDS, rabies, measles and tetanus. These compounds are also useful for the prevention of drug and alcohol withdrawal symptoms and inhibition of acquired tolerance of and dependency on opiates.

The doses depend on the desired effect, the duration of the treatment and the route of administration used; they are generally between 10 mg. and 100 mg per day orally, for an adult, with unit doses ranging from 5 mg to 50 mg of active substance.

Generally, the doctor will determine the appropriate dosage according to the age, weight and all other factors which are specific to the subject to be treated.

The following examples illustrate the compositions according to the invention.

EXAMPLE A

Gelatine capsules containing 50 mg doses of active product having the following composition are prepared according to the customary technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing 50 mg doses of active product having the following composition are prepared according to the customary technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxwethylcellulose, glycerin, titanium oxide (72-3.5-24.5) qs 1 finished 245-mg coated tablet | |

EXAMPLE C

An injectable solution containing 10 mg of active product having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water    q.s.p. | 4 ml |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

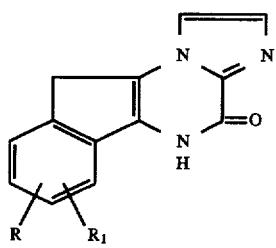

(I)

in which R and $R_1$, which are identical or different, represent a hydrogen or halogen atom or an alkyl, alkoxy, amino, acylamino, phenylureido, —N═CH—N($R_2$)$R_3$, nitro, imidazolyl, phenyl, $SO_3H$ or cyano radical, $R_2$ and $R_3$, which are identical or different, each represents an alkyl radical, wherein the alkyl and alkoxy radicals contain 1 to 4 carbon atoms in a linear or branched chain and the acyl portions contain 2 to 5 carbon atoms, the pure E or Z isomers and the mixtures of these isomers when R and/or $R_1$ represent a radical —N═CH—N($R_2$)$R_3$, or a salt of a compound of formula I.

2. A compound of formula (I) according to claim 1, wherein either: (1)R represents a hydrogen atom and $R_1$ is in position 7, 8 or 9 and represents a hydrogen or halogen atom or an alkyl, alkoxy, amino, acylamino, phenylureido, —N═CH—N($R_2$)$R_3$, nitro, imidazolyl, phenyl or $SO_3H$ radical; or (2)R represents a halogen atom and $R_1$ represents a halogen atom or a nitro radical.

3. A process for preparing a compound of formula (I) according to claim 1, comprising cyclizing a derivative of formula:

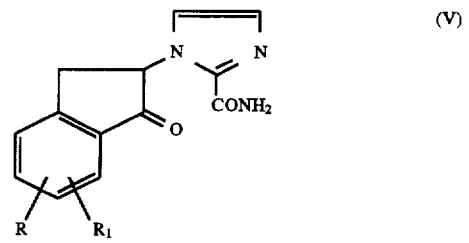

(V)

in which R and $R_1$ have the same meanings as in claim 1, isolating the cyclized product obtained, and optionally converting said compound to a salt.

4. A pharmaceutical composition, comprising an effective amount of a compound of claim 1 or a salt thereof together with a pharmaceutically acceptable carrier.

5. A pharmaceutical composition, comprising an effective amount of a compound of claim 2 or a salt thereof together with a pharmaceutically acceptable carrier.

6. A pharmaceutical composition for antagonizing a AMPA receptor, comprising an antagonistic effective amount a compound of claim 1 or a salt thereof, together with a pharmaceutically acceptable carrier.

7. A pharmaceutical composition for antagonizing a NMPA receptor, comprising an antagonistic effective amount a compound of claim 1 or a salt thereof, together with a pharmaceutically acceptable carrier.

8. A compound of formula (II):

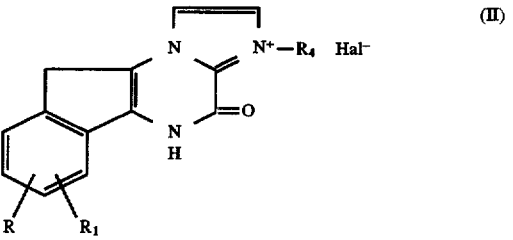

(II)

in which R and $R_1$, which are identical or different, represents a hydrogen or halogen atom or an alkyl, alkoxy, amino, acylamino, phenylureido, —N═CH—N($R_2$)$R_3$, nitro, imidazolyl, phenyl, $SO_3H$ or cyano radical, $R_2$ and $R_3$, which are identical or different, each represents an alkyl radical, $R_4$ represents an alkyl radical and Hal represents a halogen atom, wherein the alkyl and alkoxy radicals contain 1 to 4 carbon atoms in a linear or branched chain and the acyl radicals contain 2 to 5 carbon atoms.

* * * * *